(12) United States Patent
Farone

(10) Patent No.: US 9,095,694 B2
(45) Date of Patent: Aug. 4, 2015

(54) METHOD AND MORPHOLOGICALLY ADAPTABLE APPARATUS FOR ALTERING THE CHARGE DISTRIBUTION UPON LIVING MEMBRANES WITH FUNCTIONAL STABILIZATION OF THE MEMBRANE PHYSICAL ELECTRICAL INTEGRITY

(75) Inventor: William Farone, Irvine, CA (US)

(73) Assignee: Gradient Technologies LLC, Memphis, TN (US)

( * ) Notice: Subject to any disclaimer, the term of this patent is extended or adjusted under 35 U.S.C. 154(b) by 639 days.

(21) Appl. No.: 13/360,416

(22) Filed: Jan. 27, 2012

(65) Prior Publication Data

US 2012/0149969 A1    Jun. 14, 2012

Related U.S. Application Data

(60) Continuation of application No. 12/606,052, filed on Oct. 26, 2009, now Pat. No. 8,105,228, which is a division of application No. 11/469,346, filed on Aug. 31, 2006, now Pat. No. 7,608,035.

(51) Int. Cl.
*A61N 2/02* (2006.01)
*A61N 2/00* (2006.01)
*A61N 2/06* (2006.01)

(52) U.S. Cl.
CPC .............. *A61N 2/006* (2013.01); *A61N 2/008* (2013.01); *A61N 2/02* (2013.01); *A61N 2/06* (2013.01)

(58) Field of Classification Search
CPC ......... A61N 2/006; A61N 2/008; A61N 2/02; A61N 2/06; A61N 2/00; A61N 2/004
USPC ........................................................ 600/9–15
See application file for complete search history.

(56) References Cited

U.S. PATENT DOCUMENTS

| 4,537,181 A | 8/1985 | Shalhoob |
| 5,312,321 A | 5/1994 | Holcomb |
| 6,245,006 B1* | 6/2001 | Olson ............................. 600/15 |
| 6,383,129 B1 | 5/2002 | Ardizzone |
| 6,461,288 B1* | 10/2002 | Holcomb .......................... 600/9 |
| 2003/0092960 A1* | 5/2003 | Holcomb .......................... 600/9 |

* cited by examiner

*Primary Examiner* — Samuel Gilbert
(74) *Attorney, Agent, or Firm* — Thomas G. Peterson; Nicholas J. Landau; Bradley Arant Boult Cummings LLP

(57) ABSTRACT

A morphologically adaptable apparatus for altering the charge distribution upon living membranes with functional stabilization of the membrane physical electrical integrity, the apparatus having a quadripolar, circular, center charged, energy balanced magnetic device in a four (4) magnet array of alternating polarity in which the magnetic poles are in multiple planes and are separated by a predetermined distance which provide an effective magnetic sphere of influence on all adjacent poles to suppress the firing of action potentials of mammalian sensory neurons.

16 Claims, 8 Drawing Sheets

Diagram of Quadrapolar Array

METHOD AND MORPHOLOGICALLY ADAPTABLE APPARATUS FOR ALTERING THE CHARGE DISTRIBUTION UPON LIVING MEMBRANES WITH FUNCTIONAL STABILIZATION OF THE MEMBRANE PHYSICAL ELECTRICAL INTEGRITY

CROSS-REFERENCE TO RELATED APPLICATIONS

This application is a continuation of U.S. Ser. No. 12/606,052, filed on Oct. 26, 2009 (currently pending). U.S. Ser. No. 12/606,052 is a division of U.S. Ser. No. 11/469,346, filed Aug. 31, 2006 (now U.S. Pat. No. 7,608,035). The contents of U.S. Ser. Nos. 12/606,052 and 11/469,346 are incorporated by reference herein in their entireties.

BACKGROUND OF THE DISCLOSURE

1. Field of the Disclosure

The present disclosure relates to magnetic devices for therapeutic application for mammals, and more particularly to a static field, quadripolar magnetic treatment device with flux return means and a focusing means to increase the intensity, focus and gradient of the field for placement against or in proximity to the mammal's body or surface. The present disclosure further relates to methods of use and construction of such magnetic treatment devices for the use of or treatment of various diseases, complications and disorders such as, but not limited to, a) acute and chronic pain, b) cardiac dysfunction, c) seizure disorders, d) pain and edema sustained in minor burns, e) insect bites and bee stings, f) potentiation of pharmaceuticals and focusing and for concentrating the drug to the active site, g) protection of transplant organs, h) treatment of movement disorders, i) control of edema and pain as well as speed healing following surgical procedures, j) control of pain and sludging of sickled cells in sickle cell disease, k) foot pain and discomfort, l) treatment of pain and other dysfunctions, m) potentiation of epidural anesthesia and epidural analgesia, n) Protection from cell injury and death following cell insults such as contusion, hypoxic stroke and infection, o) control of nausea and vomiting associated with pregnancy, motion, and chemotherapy, p) prevention of fertilization of ovum by sperm, q) cumulative trauma disorder in the workplace, r) a magnetic placebo which has no biological activity yet is magnetic and has all characteristics of the authentic device except the alternating poles and a significant field gradient.

2. General Background of the Disclosure

Magnetic fields have been applied to the human body for various therapeutic purposes for many centuries. For example, magnetic medical treatment devices for application against selected portions of the human body are disclosed in U.S. Pat. Nos. 3,921,620 and 5,941,902; method and apparatus for suppressing neuron action potential firings are disclosed in U.S. Pat. No. 5,312,321; magnetic plasters for improving circulation are disclosed in U.S. Pat. No. 4,489,711; magnetic fields for stimulation of bone growth are disclosed in U.S. Pat. No. 4,105,017; and magnetic stimulation of nerve cells has been accomplished with devices such as the Cadwell Magneto-Electric Stimulator (MES-10) manufactured by Cadwell Laboratories, Inc. of Kennewick, Wash.

Various disease states, tissue and organ malfunction may be the result of loss of membrane stability and normal permeability. These membranes may be cellular or intracellular, but in any case represent malfunction of excitable tissue. This malfunction of excitable tissue may be due to alteration of ion channel function. These various disease and states of malfunction may also be related to alteration of receptor sites or agonist sites of enzymes and/or other such dynamic systems within living organisms and more particularly the human animal. A great variety of symptoms and malfunctions may occur, such as, but not limited to, the above listed disease and/or disorder states. Many types of ailments, including chronic pain, poor localized blood flow, cerebral edema and certain seizures and injuries cannot be successfully treated with conventional drug, physical therapy or surgical therapies. Because such ailments are often untreatable with conventional therapies, there is a need for alternative therapies that relieve these previously untreatable or poorly treatable conditions.

BRIEF SUMMARY OF THE DISCLOSURE

A therapeutic static magnetic treatment device adapted for placement of magnetic flux generator poles applied such that the treatment device may be applied to the mammal as described herein for the various applications revealed herein. The device comprises a plurality of static magnetic bodies. In one implementation, the device further comprise four such magnetic bodies each with a positive and negative pole in each head of the applications, having at least two positive and two negative magnetic poles substantially in a single plane, the magnetic poles being oriented to define the four vertices of a quadrilateral shape, the two positive poles defining opposite diagonal vertices, and the two negative poles defining opposite diagonal vertices of the quadrilateral shape, each of the magnetic poles being magnetically attracted by the oppositely charged poles and being magnetically repelled by the like charged poles.

A method and apparatus for altering the charge distribution upon living membranes with functional stabilization of the membrane physical electrical integrity is disclosed. In exemplary implementations, the method comprises providing a magnetic device in a four (4) magnet array of alternating polarity in which the magnetic poles are separated by a predetermined distance to provide an effective 3-dimensional symmetric magnetic sphere of influence at the desired site of action from the magnetic fields of all adjacent poles; positioning the device adjacent the living membranes to suppress the firing of action potentials of mammalian sensory neurons; wherein the magnet array is altered to focus the magnetic sphere at different depths.

In another implementation the plurality of magnets may be positioned so that positive and negative poles are aligned in different planes or away from one another such that the quadrilateral shape lies along a curved surface with sufficient strength to achieve the same effective magnetic field at the site of pain or cell damage as similar number of magnets of different size in a single plane in order to conform the shape of the magnetic field to the position of treatment.

In a further implementation, a morphologically adaptable apparatus for altering the charge distribution upon living membranes with functional stabilization of the membrane physical electrical integrity is disclosed. The apparatus comprises a quadripolar, magnetic device in a four (4) magnet array of alternating polarity in which the magnetic poles are separated by a predetermined distance which will provide an effective 3-dimensional symmetric magnetic sphere of influence at the desired site of action from the magnetic fields of all adjacent poles to suppress the firing of action potentials of mammalian sensory neurons; a conductive fluid flux focusing medium above and around the magnetic array to focus the magnetic field at the site of the membranes; a non-conductive fluid flux return medium below the magnetic array to allow the magnetic field to penetrate the site of the membranes to be treated; and said 3-dimensional symmetric magnetic sphere is perpendicular to the neuron current flow direction.

In another implementation, the method and apparatus has magnets that vary in size to alter the location of the gradient of the magnetic field to set the steepest magnitude of the gradient at the sensory neuron.

In a further implementation, the magnets are oriented to focus the magnetic field at a single point to alter the location of the gradient of the magnetic field at the sensory neuron.

In another implementation, the method and apparatus has a 3-dimensional symmetric magnetic field is at least 1.5 mT at the site of the neurons.

In further implementations, the method and apparatus further comprises the step of providing a conductive fluid flux focusing medium above and around the magnetic array to focus the magnetic field at the site of the membranes containing neurons.

In further implementations, the method and apparatus further comprises the step of providing a non-conductive fluid flux return medium below the magnetic array to allow the magnetic field to penetrate to the site of the membranes to be treated. In another exemplary implementation, the flux focusing medium may comprise a flux focusing ring or other medium and the flux return medium may comprise a flux return ring or other medium wherein said flux return ring returns at least 50% of magnetic field to membrane site containing neurons.

In a further implementation, the method and apparatus provide a steep field gradient from the magnet array of alternating polarity at the site of the neurons. In this implementation of the method, said steep field gradient from said magnet array is perpendicular to the direction of neuron current flow.

The apparatus and method may aid diseases, disorders, complications and conditions that are selected from the group consisting of acute and chronic pain, cardiac disorders, potentiation of pharmaceuticals, movement disorders, potentiation of anesthesia, nausea control, and trauma.

In exemplary implementations, the magnets can all be replaced by electromagnets where the magnetic field is obtained by AC running through wires that are wrapped into a coil. the individual magnets are created by varying or alternating current conducted through wires in the form of coils that act as electromagnets.

In a further implementation, the method and apparatus provides applying a symmetric quadripolar, three dimensional magnetic flux field which is focused and balanced to the human body to stabilize excitable membranes and thereby reduce pain and edema associated with acute injury, inflammation or surgical procedure and to decrease wound healing time wherein the field gradient is steep and at least 1.5 mT at the site of the neurons.

In a further implementation, a conductive gel above the magnets to serve as a focusing ring, and a gel below the magnets as a non-conductive gel to allow the magnetic field to pass unimpeded is provided. The conductive gel above the magnets deflects the field as a means of increasing or focusing the magnetic field down in the site of treatment.

In an exemplary implementation, the devices provides a static magnetic device for production of a magnetic field for treatment of pain disorders, such a device being powered by a particular static magnetic field and having, inter alia, an alternating polarity, quadripolar array which generates a 3 dimensional, steep field gradient (greater than 0.25 tm/mm at the site of action) with a homogenous field.

In yet another implementation, the apparatus provides an alternating, quadripolar array in which each of the poles is in the shape of two cones joined at the directrix of the cone with the vertex of the two cones lying in a perpendicular axis of a circular directrix.

In a further implementation, the plurality of magnets are so positioned that the positive and negative poles are aligned in different planes or away from one another with sufficient strength to achieve the same effective magnetic field at the site of pain or cell damage.

In another implementation, the device provides a conductive gel above the magnets to serve as a focusing medium to deflect the field to the site of pain, and a gel below the magnets as a non-conductive gel to allow the magnetic field to pass unimpeded.

Furthermore, there is taught a method and apparatus for altering the charge distribution upon living membranes with functional stabilization of the membrane physical electrical integrity.

In yet another implementation, a device that alters the stability of excitable membranes and other charged structures and systems in order to treat ailments in mammals is provided.

A further implementation presents a global technique for controlling the physical and electrical stability of irritable membranes (either cell walls or intra-cellular organelles) and altering receptor sites, i.e. enzymes, hormones and/or drugs.

There is further taught a device in which the desired biological effects are directly related to the magnitude of the gradient in the x, y and z axis and therefore the magnitude of the vector or summation gradient.

A further implementation provides a device which contains a flux return medium on the back surface away from the body surface which is designed to return the magnetic flux thereby altering (increasing) the strength and gradient without materially altering the center charge symmetry and homogeneity of the 3 dimensional steep gradient field.

A further implementation of the device provides a flux focusing medium surrounding the (static) magnetic poles on the outer perimeter stationed substantially midway between the top and bottom of the pole surrounding static magnetic poles on the outer perimeter stationed substantially above the magnets on the side away from the site of action to direct the magnetic field flux back toward the site of action to increase the field and the field gradient. Attachment means is provided to hold the focusing medium to the outer perimeter of the poles throughout the total support means.

Another implementation provides a static magnetic pole of like polarity on the outer surface of each of the poles of the focusing magnet such that the top of the focusing magnet is oriented to the geometric side of the pole, for example such that the axis of two magnets form a 45 to 90 degree angle or a 90 to 135 degree angle. The focusing magnet comprises a static magnetic pole.

In another implementation, a static magnetic pole of like polarity on the outer surface of the flux focusing ring adjacent to, for example, each of the 4 poles of the device (focusing magnet) such that the end or top of the focusing magnet is oriented to the geometric side of the pole such that the axis of the two magnets form a 45 to 90 degree angle. The focusing magnet comprises a static magnetic pole. The angle of the focusing magnet is such that the axis forms a 45 to 90 degree angle on the body surface side and a 90 to 135 degree angle to the surface away from the body.

In another implementation, one can control the focusing of each magnet with a smaller and weaker magnet than the primary pole such that the focusing medium containing magnets can focus and balance the symmetry of the therapeutic field.

A further implementation reveals a method of design and manufacture of an inexpensive, center charged and homogeneous static magnetic flux magnet.

In one implementation the plurality of magnet bodies in each device comprises four lightweight, intense field static magnets, the static magnetic poles being the shape of a cylinder or in a further implementation in the shape of two cones joined at the directrix of the cone with the vertex of the two cones lying in a perpendicular axis of the circular directrix such that the vertex of the double cone shaped magnetic bodies may all be tilted toward the midline (on the side facing the animal body) such that the peak or vertex being pulled toward the midline will give a more steep field gradient.

In an additional implementation the device contains a flux return medium on the back surface away from the body surface which is designed to return the magnetic flux thereby increasing the strength and gradient without altering the center charge symmetry and homogeneity of the 3 dimensional steep gradient field.

In a further implementation, a flux focusing medium surrounds, for example, four static magnetic poles on the outer perimeter stationed midway between the top and bottom of the pole at the junction of the base of the two cone shapes which join at the directrix of the cone.

On the outer surface of each of the poles of the disclosure attached to the flux focusing ring is a small focusing cylindrical magnet oriented to the geometric side of the pole such that the axis of two magnets form a 45 to 90 degree angle (Focusing magnet/Magnet pole=¼ in size). In another implementation the containment means may be plastic which covers the entire implementation. The size of the device is dictated by the application, but averages about 1×¼ inches in the round.

In a further implementation, a method of adding a plastic material to a permanent magnet amalgam along with a proprietary silica colloid and curing the amalgam under the influence of a strong, center charged homogenous magnetic field is disclosed.

The accompanying drawings, which are incorporated herein and constitute a part of this specification, illustrate implementations of the disclosure, and together with the description, serve to explain the principles of the disclosure. Another implementation provides a magnetic device which has the flexibility to treat human cells, while not necessarily lying in a single plane, but more in adapting to the specific contours of the cells being affected; i.e. to make the device morphologically adaptable in its multiple applications.

Definitions:

In accordance with the present disclosure and as used herein, the following terms are defined with the following meanings, unless explicitly stated otherwise.

The term "mammal" refers to any of various warm-blooded vertebrate animals including those in the class Mammalia, and includes humans.

The term, "Tesla" refers to a unit of magnetic flux density or magnetic field intensity in the International System of Units equal to the magnitude of the magnetic field vector necessary to produce the force of one Newton on a charge of one coulomb moving perpendicular to the direction of the magnetic field vector with a velocity of one meter per second.

The term, "grease" refers to a thick oil or viscous substance.

The term "gradient" refers to the rate at which a physical quantity, such as temperature or pressure, increases or decreases relative to change in a given variable, especially distance. The term may also refer to a vector having coordinate components that are the partial derivatives of a function with respect to its variables.

The term "summation gradient" refers to the vector sum of the magnetic field from all magnets in the array.

DETAILED DESCRIPTION

Figure 1:
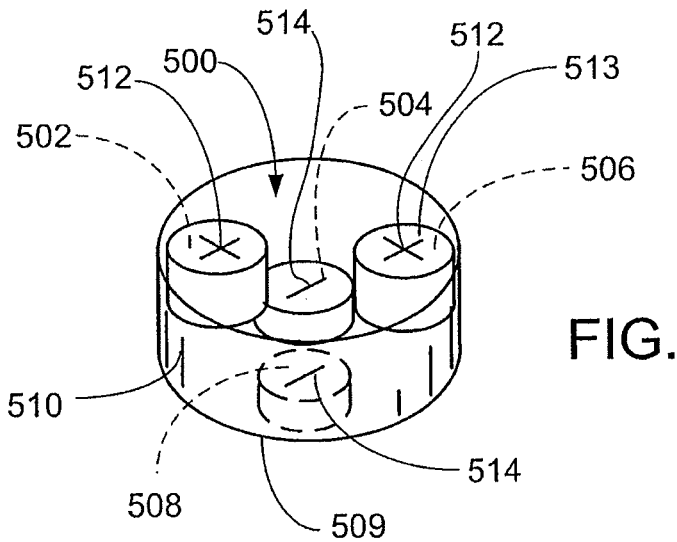
FIG. 1 illustrates an overall view of an implementation of the magnetic device.

Before explaining the present disclosure in detail, it is to be understood that the disclosure is not limited to the particular implementations and that it can be practiced or carried out in various ways.

Device

Devices are taught with magnetic poles of alternating polarity directed toward the site of membranes or neurons to be treated in which the poles may all be tilted toward (or away from) the midline (on the side facing the mammal body) such that the peak or vertex position toward the midline will vary (or sharpen the angle of) the field gradient.

There are taught methods which provide devices with magnetic poles of alternating polarity directed toward the site of membranes or neurons to be treated in which the shape of the magnetic bodies can be changed by constructing any number of the magnets to be of different size, magnetization, or orientation attached to the flux return ring which faces away from the mammal body. The vertex may be tilted toward the midline (on the side facing the mammal body) such that the peak or vertex position toward the midline will alter the field gradient.

Improved Morphologically Adaptable Implementations

Reference is now made to several implementations of the device that will be discussed below in detail in reference to FIGS. 1 through 19. In general, one or more variations to the current parallelogram with attendant magnetic pole modifications will demonstrate the range (pole strength and distance) of (a) alternative single plane configurations; (b) an electromagnetic configuration; (c) a saddle configuration; (d) a two (2) plane configuration; (e) the use of a gel as a replacement for and/or compliment to the focusing ring; and (f) a countercurrent option to the mini-MagnaBlocs to be included in the magnetic treatment device (U.S. Pat. No. 6,461,288) as an alternative method for drug potentiation.

In the implementations, there is provided an effective magnetic field at the site of pain. Electromagnetic fields benefit from a concept known as superposition. A simple example can illustrate this with light which is an electromagnetic field. If one would shine two identical flashlights on a spot the field strength is the same as if one used a flashlight with twice the illumination. If one uses one that is 50% and another that is 150% of the illumination of the original two the spot still is the same field intensity.

The magnetic arrays taught in this patent can be used wherever the arrays described in U.S. Pat. Nos. 5,312,321 and 6,461,288 can be used.

Thus, in the disclosed implementations any two opposing magnets can be moved away from the other two as long as there is an adjustment their magnitude to make the "spot" at the point of action the same. If one moves two in a plane above the other two, the two in the high plane need to be stronger. If one moves two in the plane further away from the center, the two that are further away need to be stronger.

In other implementations, the magnets can all be replaced by electromagnets where the magnetic field is obtained by AC running through wires that are wrapped into a coil. Usually this coil is wrapped on a piece of ferromagnetic material and the most convenient form is a toroid (dough nut shape) because the field through the center of the toroid acts up and down through the hole giving the action of a regular permanent magnet. Winding the coil in a cylindrical shape either around a core or simply arranged as a cylinder can also provide the positive and negative magnetic poles at the ends of the cylinder. The implementation of the "saddle" is for wrists, ankles, etc. where it will be convenient to bend two of the magnets respective to the plane of the other two to create the equivalent field at the site of action.

The focusing ring can be replaced by a conductive gel above the magnets. The gel below the magnets is preferentially non-conducting to allow the field to pass unimpeded. A gel above the magnets (away form the site of action) will deflect the field and can be molded like the focusing ring. It is foreseen that the type of gel to be most effective would be a gel product of the type offered by McMaster-Carr, disclosed in the 2004 company catalog 110.

In these implementations, the magnets can also be held in the same ceramic or plastic housing. The magnets may look like one magnet when this is done, but each magnet has a unique north and south pole. If magnets are not separated in space as required by the disclosure, one cannot maintain the quadripolar arrangement. Even though the magnets are in one "structure," they are still separate magnets and the magnets can take all the configurations noted above.

Turning now to the Figures which illustrate the morphologically adaptable implementations, FIGS. 1 though 9 illustrate exemplary implementations of the magnetic device 500 illustrated in FIG. 1. As illustrated first in FIG. 1, magnetic device 500 includes a plurality of at least four magnetic bodies 502, 504, 506, 508, that are oriented and contained within a housing 510 that can be maneuvered manually without upsetting the arrangement and orientation of the magnetic bodies 502 through 508. In general, and depending on the specific implementation which will be discussed below, each of the magnetic bodies comprises a cylindrical, center-charged permanent magnet. The magnets may or may not be, depending on the implementation, of equal strength, and set at equal planes within the housing 510. Magnets across from one another will always have the same polarity. In one implementation magnets opposite one another are of equal strength; for example 502 and 506 will have the same strength and in another implementation magnets 502 and 506 may have different strengths. Each of the magnetic bodies are arranged so that there are opposing positive and negative magnetic poles. When the magnets are in a flat plane they will not be of equal strength. In a different implementation with magnets of equal strength , the magnets will not be in a flat plane. Collectively, the four magnetic bodies define a magnetic octapole.

Turning first to FIG. 1, there is provided the magnetic device 500 having four magnetic bodies 502, 504, 506, and 508. The four magnetic bodies are contained and held fixed within a housing 510. In this implementation, as seen in views in FIGS. 82 and 83, the bodies 502 and 506 are opposing bodies, each having a positive pole 512 and a negative pole 514, with bodies 502 and 506 positioned within the upper plane of the housing 510, each having a positive pole 512 on their upper surface 513 and a negative pole 514 on their lower surface 509. The bodies 504, 508 comprise bodies which are smaller in dimension and include a positive pole 512 on their lower most surface 509 and a negative pole 514 on their upper surface 513. In effect, each magnetic body contains both a positive and negative pole. This particular arrangement of poles provides the desired quadripolar configuration. The magnetic fields of 502, 506, 504, 508 will combine symmetrically in three dimensions in the space above the magnets according to the size and magnetization of the magnets.

Figure 4:
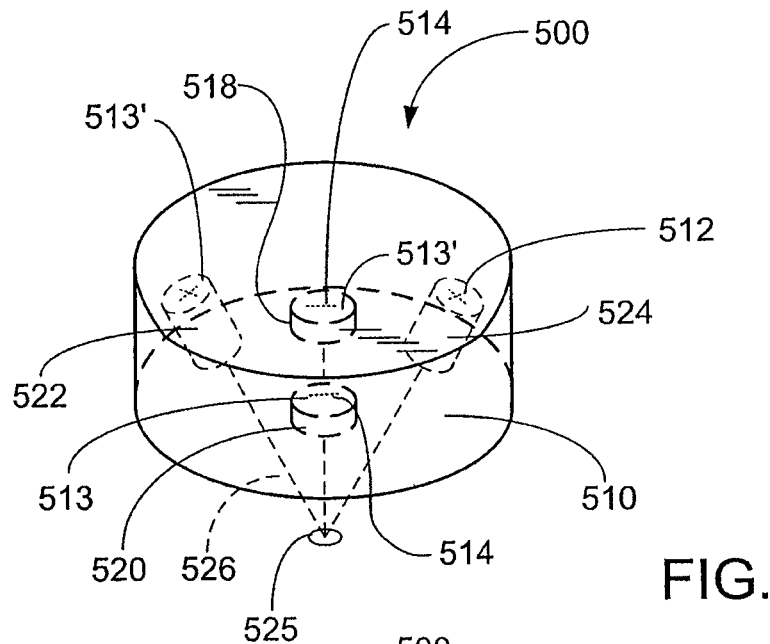
FIG. 4 illustrates an overall view of an alternative implementation of the magnetic device illustrated in FIG. 1.
Figure 5:
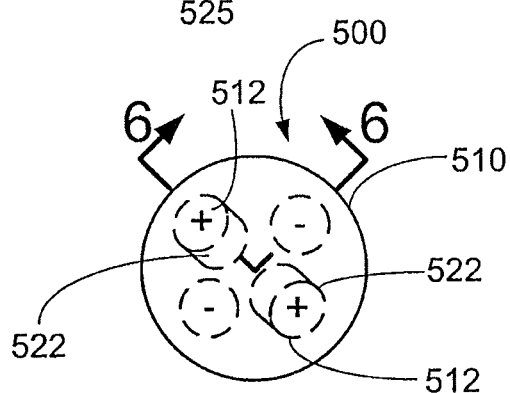
FIG. 5 illustrates a top view of FIG. 4 thereof.
Figure 6:
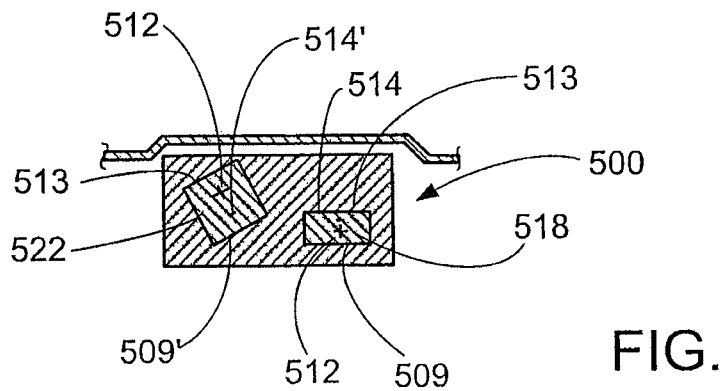
FIG. 6 illustrates a cross-section view through lines 4-4 in FIG. 5 of the alternative implementation of the improved magnetic device.
Figure 7:
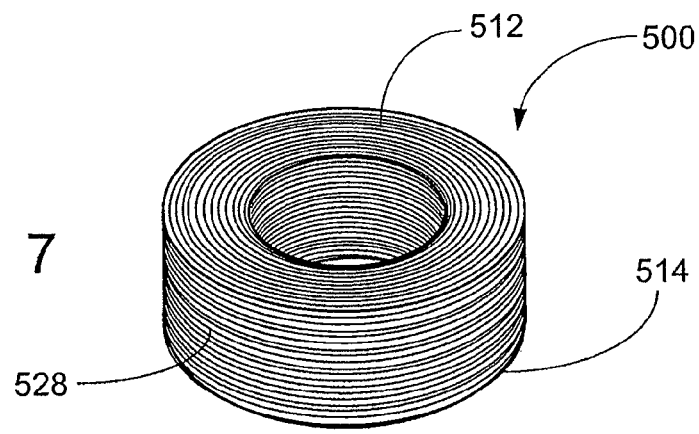
FIG. 7 illustrates an overall view of a second implementation of the magnetic device illustrated in FIG. 1.

Turning next to the implementation illustrated in FIGS. 4 through 6, again there is provided four magnetic bodies set fixed within housing 510. However, in this implementation, there is provided two small magnetic bodies 518, 520, oriented such that there is a negative pole 514 on the upper surface, each having the negative pole 514 on their upper surface 513, and a positive pole 512 on their lower surface 509. In this implementation there is also provided an opposing pair of larger magnetic bodies 522, 524 positioned at an angle within housing 510, and opposing one another, each body 522, 524 having a positive pole 512 on their upper surfaces 513, and a negative pole 514 on their lower surfaces 509. As seen in FIG. 4, the position of the bodies within the housing in this fashion allows the combined magnetic field to be focused at point 525, as illustrated by phantom lines 526. The positioning the magnetic bodies in this alignment maintains the quadripolar configuration of the magnets that allows control over the steep magnet field gradient.

Figure 2:
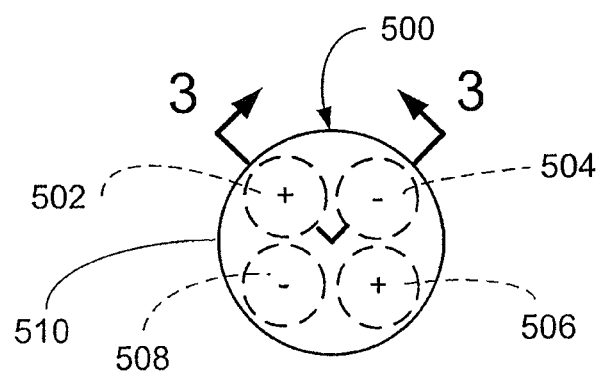
FIG. 2 illustrates a top view of the magnetic device illustrated in FIG. 1.
Figure 3:
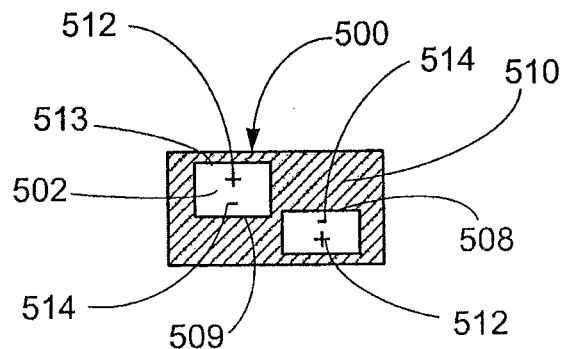
FIG. 3 illustrates a cross-section view through lines 2-2 of FIG. 2 of the magnetic device.

In FIG. 7 through 10, the magnetic bodies 502 through 508 are charged similarly as the bodies described in FIGS. 1 through 3, and are positioned within housing 510 in the identical fashion. However, in the implementation provided in FIGS. 7 through 10, each of the bodies are contained within a wire coil 528, wound tightly around each of the bodies, with the coil having a positive pole 512 and negative pole 514, through which an electrical current could be run during use. The electric field is an alternating current and creates an electromagnetic field. The wire coils behave the same as permanent magnets as long as the current is flowing.

Figure 11:
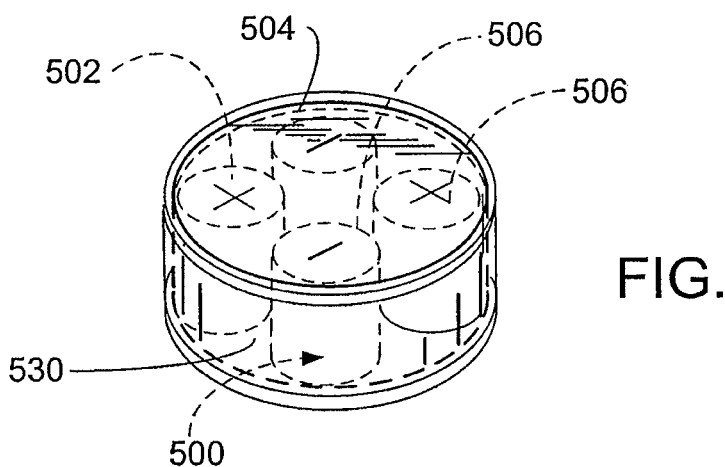
FIG. 11 illustrates a fourth alternative implementation of the magnetic device illustrated in FIG. 8.
Figure 12:
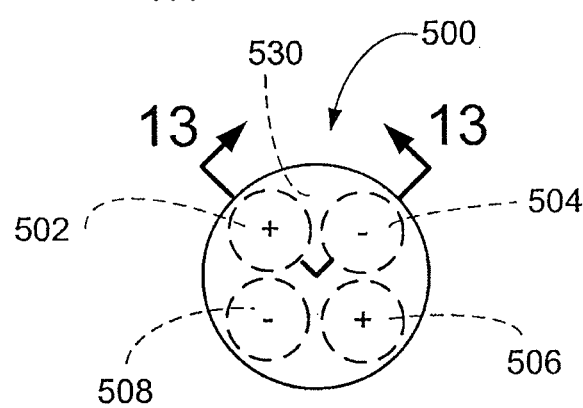
FIG. 12 illustrates a top of the device illustrated in FIG. 11.
Figure 13:
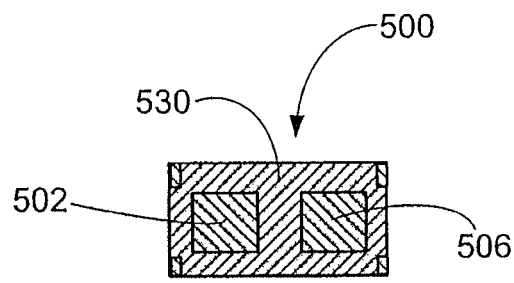
FIG. 13 illustrates a cross-section view along lines 11-11 in FIG. 12.

In FIGS. 11 through 13, the magnetic device 500 contains four charged magnetic bodies 502, 504, 506, 508, each being of identical size, with bodies 502 and 506 being positively charged while bodies 504 and 508 are negatively charged, each being positioned opposite one another. In this implementation, rather than have a solid fill between the magnetic bodies within housing 510, the fill (fluid volume 530 illustrated in FIG. 13) may be of the type of gel which was described earlier Those skilled in the art will understand that the magnetization of the four magnets need not be identical. Magnetization of a positive pair to be different than a negative pair creates a magnetic field in space whose magnitude and position is controlled by the magnetization of the pairs. Magnetic material of a wide range of magnetization is commercially available to construct such magnets.

Figure 8:
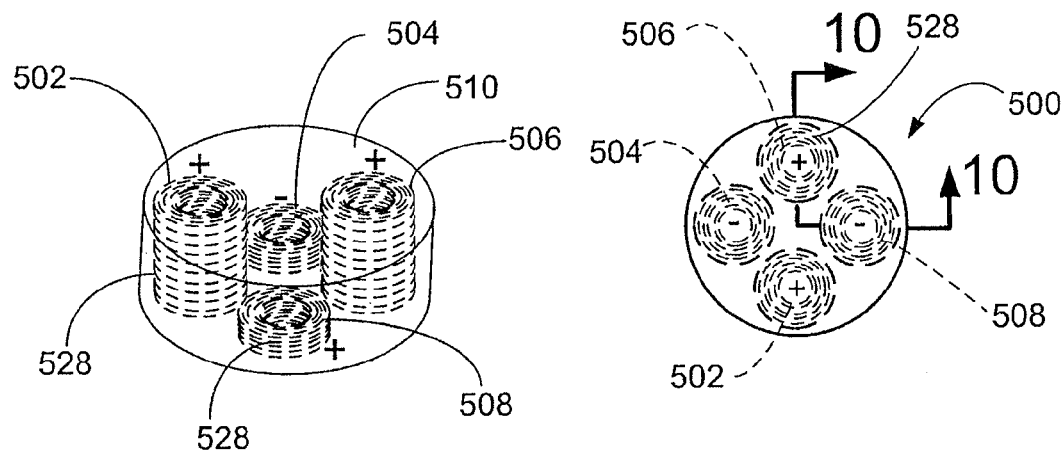
FIG. 8 illustrates a third alternative implementation of the magnetic device illustrated in FIG. 1.
Figure 9:
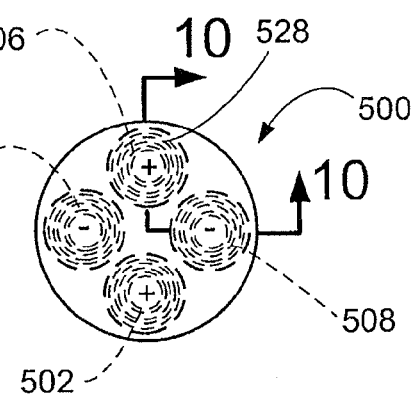
FIG. 9 illustrates a top of the device illustrated in FIG. 8.
Figure 10:
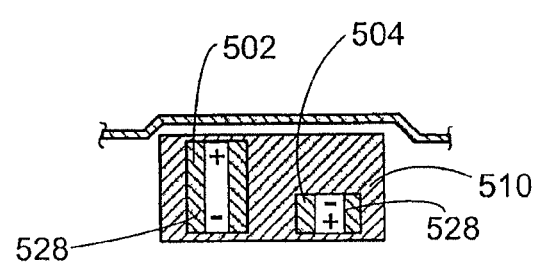
FIG. 10 illustrates a cross-section view along lines 9-9 in FIG. 9.
Figure 14:
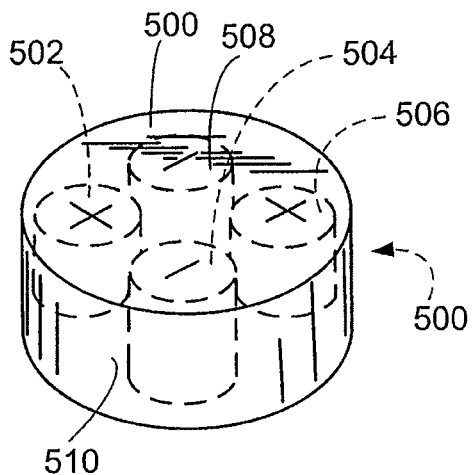
FIG. 14 illustrates a fifth alternative implementation of the magnetic device illustrated in FIG. 1.
Figure 15:
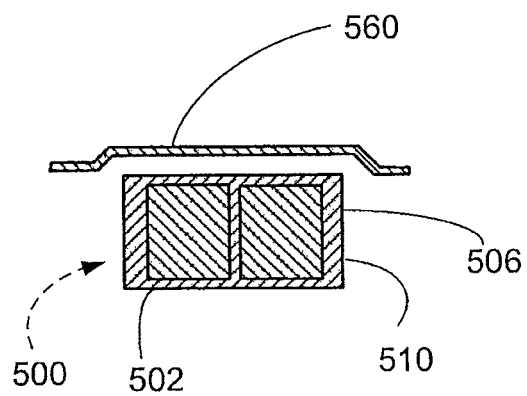
FIGS. 15 through 19 illustrate cross-section views of the magnetic device illustrated in FIG. 14.
Figure 16:
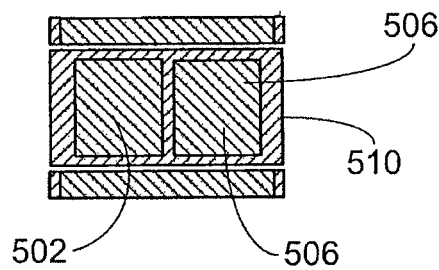
Figure 17:
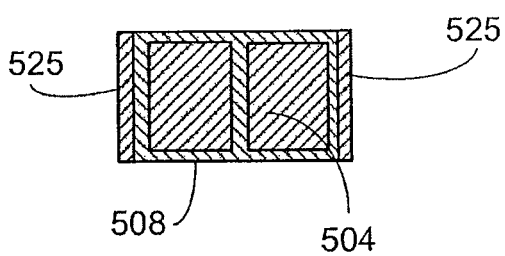
Figure 18:
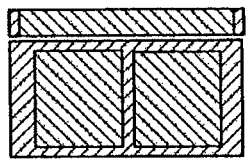
Figure 19:
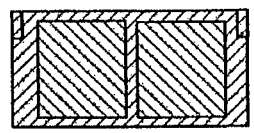

In FIGS. 14 through 19, the magnetic device 500, includes four magnetic bodies 502, 504, 506, 508, each oppositely charged positively and negatively, as with the previous implementations and contained and fixed within housing 510. FIG. 16 shows a side view of magnets 502 and 506 from FIG. 14 and FIG. 17 shows the side view of magnets 504 and 508 illustrating that they may be of different sizes within the housing 510. FIG. 15 shows the presence of a flux focusing ring which returns the magnetic field. All of the figures on this page were intended to relate to the electromagnets and to show that they can be on different size and to show wires coming out of them that can be attached to the AC circuit. FIGS. 8-10 do not show any wires to the outside circuit and only show the toroid. The rest are intended to show that electromagnets can be of cylindrical shape with various aspect ratios.

To further illustrate the disclosure described herein, some specific examples are provided as follows. The apparatus described in U.S. Pat. No. 5,312,321 has the geometry as depicted in FIG. 20.

Figure 20:
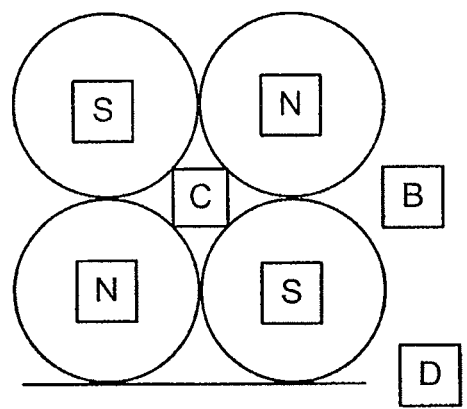
FIG. 20 illustrates a magnetic device where the magnets are all the same size and in the same plane.
Figure 21:
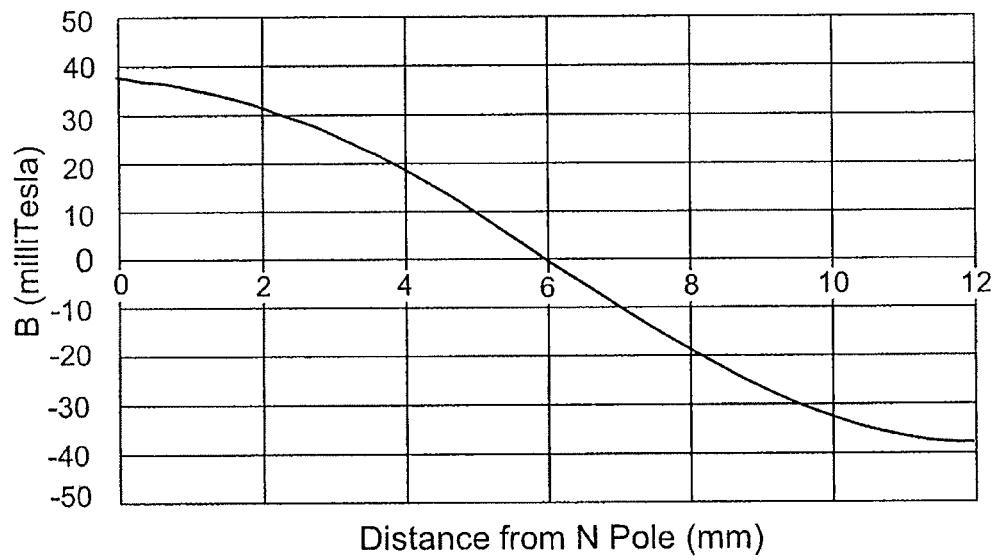
FIG. 21 illustrates the magnitude of the magnetic field of the device in FIG. 20.

In FIG. 20, the magnets are all the same size and strength. Measurements made of the field strength showed that the largest gradient, which is calculated, occurred along the line from the North to the South Pole in this configuration. There are four points at which the maximum can occur. FIG. 21 shows the magnitude of the magnetic field along the line from a North Pole to a South Pole.

The line in the FIG. 21 is calculated but the points along the line agreed with the measured points within the limitations of the Guassmeter probe (about 0.5 mm). The field gradient is the derivative of this curve and it is a negative number when the curve is decreasing and a positive number when the curve is increasing. The gradient curve for the data points presented in FIG. 21 is given below in FIG. 22.

Figure 22:
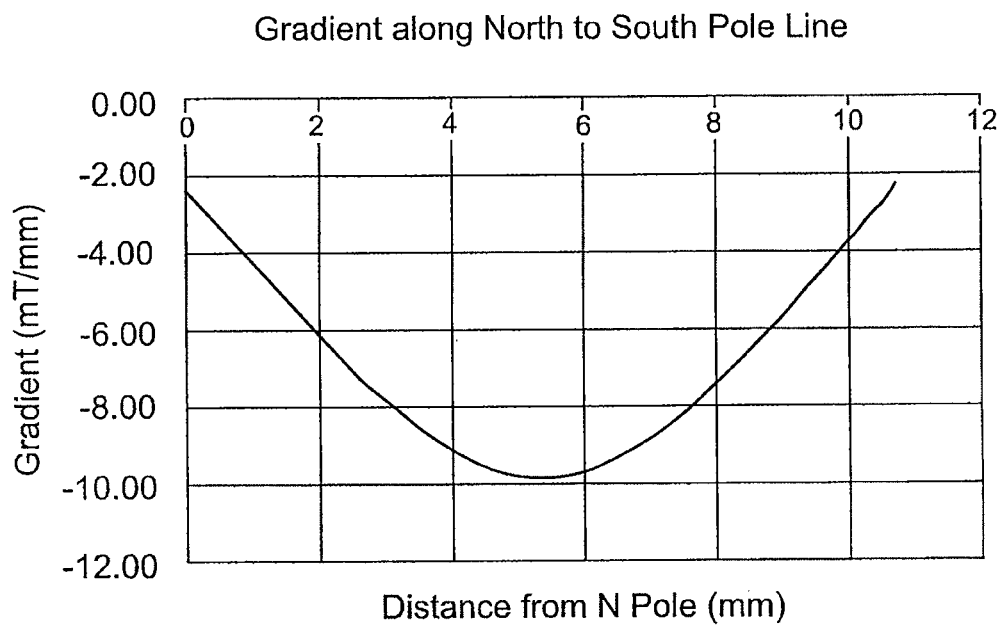
FIG. 22 illustrates the gradient of the device in FIG. 20.

As shown in FIG. 22, the gradient was largest at a point half way between the North Pole and the South Pole. The magnitude of the gradient was slightly below 10 mT per mm. The sign of the gradient indicates the direction while the magnitude indicates the effect on the charged particle.

Figure 23:
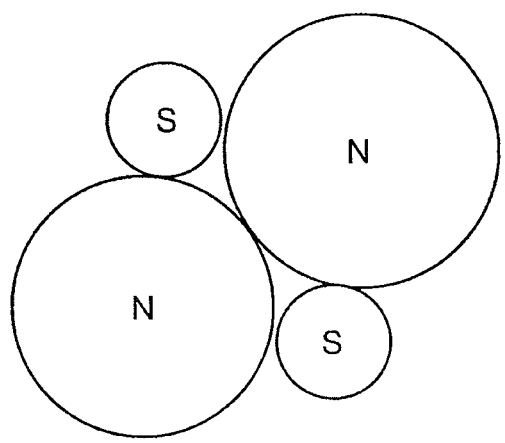
FIG. 23 illustrates an overview of an implementation of the magnetic device.
Figure 24:
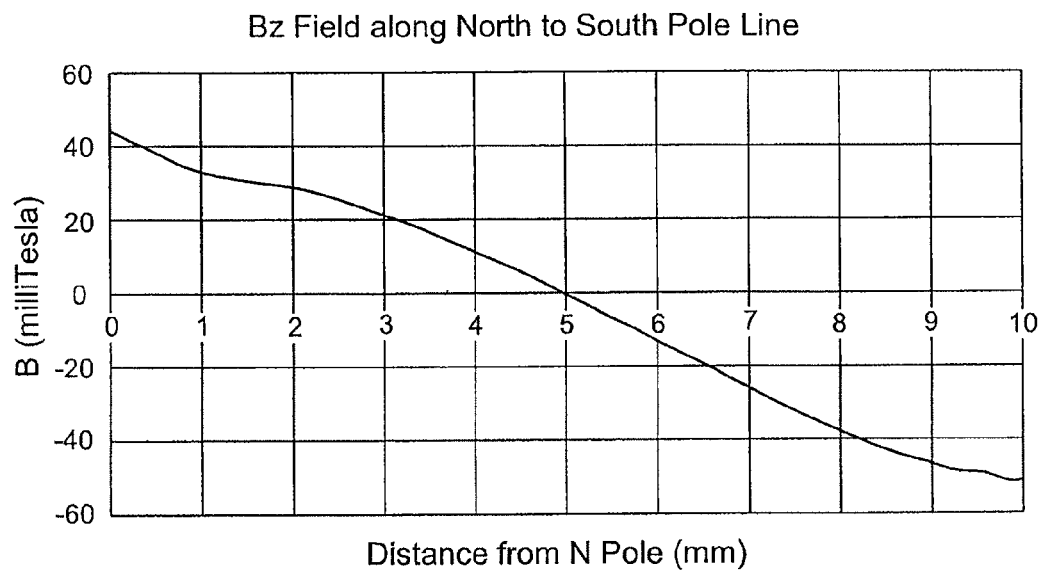
FIG. 24 illustrates the magnitude of the magnetic field of the device in FIG. 22.

The magnetic array depicted in FIG. 23 used two different size magnets which could also have different magnetization values. The magnets used in FIG. 20 were discs 12 mm in diameter and 5 mm in height. The magnets in FIG. 20 had a residual magnetization of 500 mT. In FIG. 23, the North Pole facing magnets are the same size, that is, 12 mm diameter and 5 mm height. The South Pole facing magnets in FIG. 23 were smaller (8 mm in diameter by 5 mm in height) with a residual magnetization of 1200 mT. The field along the line of a North Pole to a South Pole changed to that shown in FIG. 22. The line has been shortened to approximately 10 mm as one of the magnets in each pair was smaller. The line is not uniformly smooth but exhibited a plateau at about 1.5 mm from the North Pole and then it resumed the downward trend. The calculated gradient for the configuration in FIG. 23 is shown in FIG. 24.

Figure 25:
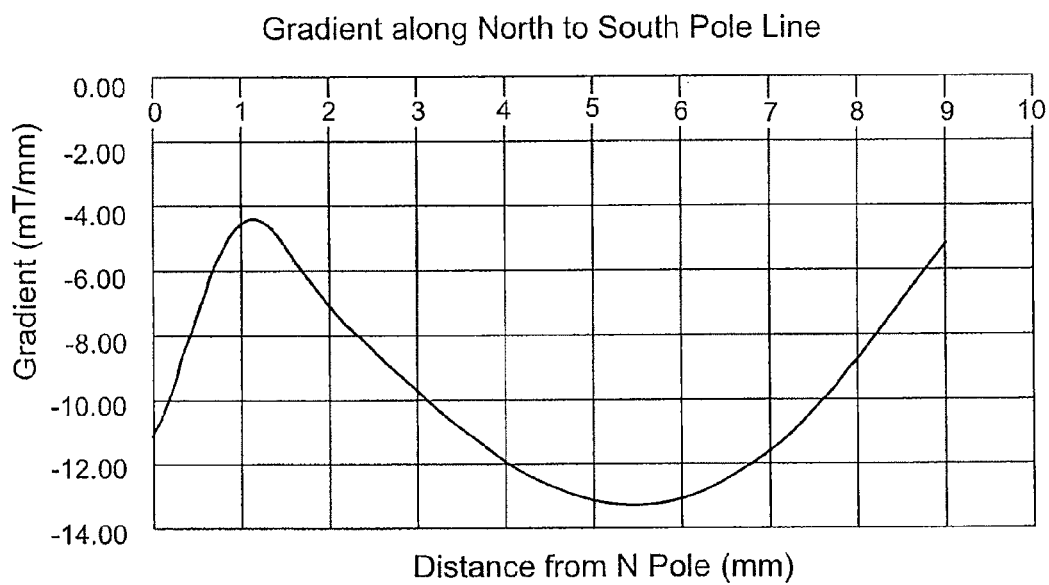
FIG. 25 illustrates the gradient of the device in FIG. 22.

As seen in FIG. 25, the magnitude of the gradient was larger than the gradient found in FIG. 23; i.e., 13 mT/mm compared to less than 10 mT/mm. The maximum value occurred closer to the South Pole allowing one to position that point in space.

FIG. 23 is only one example of possible variation in shape and design that may be utilized to provide the maximum gradient. The various shapes allows one to tailor a pattern that is specific to the range of specific neuron locations, for example, pain that runs along a lateral section of tissue would benefit from a channel configuration than a square configuration as in FIG. 20. There are a large variety of 'custom' field shapes that can be created with the designs as disclosed. These custom designs allow one to fit the apparatus to various location on a mammal or to focus the gradient at different depths in three dimensional space.

These designs with varying and different shapes allow obtaining the maximum gradient for a particular application. In FIG. 20 there are four places that are exactly at the four corners between each N-S pair. In FIG. 23, there are four points but as can be seen they are closer to the S facing poles in all four cases creating a rectangular pattern, and thus allowing a channel of greater field gradients. In this implementation, the quadrilateral of maximum gradient is not limited to a single plane and to a single square shape.

Pain Applications

A. Pain and Swelling and Wound Healing

1. Acute Pain and Edema

In an exemplary implementation, a device that alters nerve cell behavior in a manner that reduces painful sensations is provided.

An exemplary implementation provides an apparatus for applying a symmetric quadripolar, three dimensional magnetic flux field which is focused and balanced to the mammal body to stabilize excitable membranes and thereby reduce pain and edema associated with acute injury, inflammation or surgical procedure and to decrease wound healing time.

A further implementation is to provide a specialized magnetic flux field to control and reverse the swelling associated with acute injury, inflammation and surgery.

In yet another implementation provide a method for applying a therapeutic magnetic device to the human body to relieve pain, improve blood flow, decrease healing time, and reduce swelling associated with injury, surgery or acute inflammation.

2. Chronic Pain

In another implementation a device that alters nerve cell behavior in cases of chronic pain to block the spontaneous repetitive firing of the chronically malfunctioning pain fiber (for example, A-fibers and C-fibers).

A further implementation provides an apparatus for applying a symmetric, quadripolar, three dimensional magnetic flux field which is focused and balanced to the mammal body to stabilize excitable membranes and thereby reduce pain associated with the spontaneous repetitive firing of chronically malfunctioning polymodal nociceptors (afferent C-fibers and A8 fibers).

Another implementation is to provide a specialized magnetic flux field to control and speed healing of chronic slow healing wounds.

In accordance with the principles of an exemplary implementation and as broadly described herein, a therapeutic static magnetic treatment device adapted for placement against the bodies of living animals is provided. The device comprises a plurality of static magnetic bodies having at least two positive and two negative magnetic poles in a single or multiple planes, the magnetic poles being oriented to define the four vertices of a three dimensional quadrilateral shape, the two positive poles defining opposite diagonal vertices and the two negative poles defining opposite diagonal vertices of the quadrilateral shape. Each of the magnetic poles being magnetically attracted by the two oppositely charged poles and being magnetically repelled by the like charged poles.
Pain and Edema Sustained in Minor Burns, Insect Bites, Bee Stings and Minor Cuts and Abrasions.

In another implementation, magnetic devices for therapeutic application to mammal body, and more particularly to a small reusable, multiple three dimensional quadripolar treatment device optionally contained in a small sterile bandage for placement on the mammal body for control of pain and edema sustained in minor burns, insect bites, bee stings and minor cuts and abrasions.

In one implementation the apparatus provides a magnetic device that alters the permeability of the ion channels in membranes to the flow of sodium and calcium and thereby stabilizing the spontaneous firing of damaged nerve endings as well as restores the physical integrity of the membranes and stopping the abnormal loss of cellular fluid (edema).

Minor burns, insect bites, bee stings and minor cuts and abrasions are the most common injuries in our society, yet they are among the most painful and annoying injuries in our society. The only treatment for mass use is cleansing, antibiotic ointment and clean bandage.

There is a great need for a bandage which will provide a sterile cover for such wounds as well as to acutely control pain, swelling and to promote healing.

Accordingly, in a further implementation a device is provided that is small enough to be contained in a small sterile bandage inexpensive enough to be disposable and that alters pain fiber firing, repairs membrane integrity, controls edema in the area of the injury and promotes healing.

C. Foot Pain and Discomfort.

Another implementation relates to magnetic devices for therapeutic application to the mammals, and more particularly to a three dimensional quadripolar static magnetic device adapted for the utilization in the soles of shoes.

In a further implementation the containment means for the magnetic device be made of a flexible material so that placement in a shoe sole will not restrict flexibility.

In one implementation, at least one therapeutic permanent magnet device is embedded in a shoe. One permanent magnet device is embedded in the heel of the shoe sole while a second device is embedded in the portion of the shoe sole corresponding to the ball of the foot. The shoe into which the magnetic treatment devices are embedded may be of any type of footwear, as for example, running shoes, nurse's shoes or work boots.

D. Cumulative Trauma Disorder.

In another implementation, a device is provided that alters nerve cell behavior in cases of chronic pain to block the spontaneous repetitive firing of the chronically inflamed, edematous, malfunctioning pain fibers in chronic trauma disorders such as Carpel Tunnel Syndrome.

In yet another implementation, an apparatus for applying a symmetric, quadripolar, three dimensional magnetic flux field which is focused and balanced to the mammal body to stabilize excitable membranes and thereby reduce pain associated with the spontaneous pacemaker firing of chronically traumatized and malfunctioning polymodal nociceptors is provided.

Another implementation provides a specialized magnetic flux field to remove edema and control pain in a chronically traumatized tissue.

It will be apparent to those of ordinary skill in the art that the apparatus of this disclosure alters C-fibers firing both in vitro and in vivo.

In yet another implementation, the apparatus provides four static magnetic poles of alternating polarity that provides the superposition of the four magnetic fields such that the resultant steep field gradient is perpendicular to the site of action (membrane or neurons) and is of at least 1.5 mT.

This application further reveals a method and technique for placement of the devices over areas of chronic trauma such that they will alter nerve cell behavior in cases of chronic pain to block the spontaneous pacemaker firing of the chronically traumatized, enflamed, edematous, malfunctioning, pain fiber in chronic trauma disorders such as Carpel Tunnel Syndrome.

Additional implementations and advantages of the present disclosure will be set forth in part in the description that follows.

E. Control of Edema and Pain as well as Speed Healing Following Surgical Procedures and Speed Healing Rates of Chronic Slow Healing Wounds.

This application further reveals a method and technique for placement of the disclosure on post operative incisional sites for the benefit of pain control, edema control and increased healing rates.

In one implementation there is an apparatus for applying a symmetric quadripolar, three dimensional magnetic flux field which is focused and balanced to the mammal body to stabilize excitable membranes and thereby reduce pain and edema associated with acute injury, inflammation or surgical procedure and to decrease wound healing time as well as speed healing of tissue following surgical procedures and speed healing rates of slow healing wounds.

An additional implementation teaches the method of utilizing the apparatus which provides for applying a therapeutic magnetic device to the human body to relieve pain, improve blood flow, decrease healing time, and reduce swelling associated with injury, surgery or acute inflammation along with reducing or blocking swelling and speed healing following surgical procedures.

There is further provided the device which provides a specialized magnetic flux field to control and speed healing of chronic slow healing wounds.

There is further taught the methods, devices, techniques, and processes which relate specifically to control of edema and pain as well as speed healing following surgical procedures and speed healing rates of chronic slow healing wounds.

There is further taught the method which provides a device that alters cell behavior in a manner that reduces pain, swelling and speeds healing following operative procedures and of slow healing wounds and speeds healing.

1. Post Operative Treatment

In another exemplary implementation, a device that alters cell behavior in a manner that reduces pain, swelling and speeds healing following operative procedures.

There is further taught the device which provides a specialized magnetic flux field to control and reverse the swelling associated with acute injury, inflammation and surgery.

In yet another implementation, an apparatus for applying a symmetric quadripolar, three dimensional magnetic flux field which is focused and balanced to the mammal body to stabilize excitable membranes and thereby reduce pain and edema as well as speed healing of tissue following surgical procedures is provided.

Another implementation provides a method for applying a therapeutic magnetic device to the mammal body to relieve pain, improve blood flow, reduce or block swelling and speed healing following surgical procedures.

2. Chronic Slow Healing Wounds

In a further implementation, a device that alters cell behavior in a manner that reduces pain, swelling and speeds healing of slow healing wounds is provided.

An exemplary implementation provides an apparatus for applying a symmetric quadripolar, three dimensional magnetic flux field which is focused and balanced to the mammal body to stabilize excitable membranes, improve blood flow, relieve pain, reduce swelling and speed healing rates of slow healing wounds.

A further implementation presents an application of the quadripolar array in a microscopic implementation contained within a housing designed to be placed in the epidural space and other body cavities.

F. Potentiation of Epidural Anesthesia and Epidural Analgesia.

There is taught the implementation of implantable quadripolar devices which contain flux focusing and flux return means or medium.

There is further taught the application of the quadripolar array in a microscopic implementation contained in a housing designed to be placed in the epidural space and other body cavities There is further taught the methods, devices, techniques, and processes which relate specifically to potentiation of epidural anesthesia and epidural analgesia.

There is further taught the methods, devices, techniques, and processes which specifically relates to a method for using, quadripolar, circular, center charged, energy balanced magnetic device in a four (4) magnet array of alternating polarity in which the magnetic poles are separated only by a distance which will allow a magnetic sphere of influence on all adjacent poles to suppress the firing of action potentials of mammalian sensory neurons.

There is further taught the method which provides for applying a magnetic field which is particular to this device, to a nerve cell such that it alters nerve behavior by deflecting the ions that cause neuron firing by applying a steep field gradient of at least 1.5 mT perpendicular to the flow of charge.

There is further taught the method which provides applying the magnetic field to the dorsal root ganglia by placing the device in the epidural space adjacent to the dorsal root.

There is further taught the method which provides for the helical design of the housing so as to allow impingement of the dorsal root regardless of the rotation of the housing.

There is further taught the method which provides for a magnetic device with a configuration of static magnets with a particular pole design that, when placed close to a nerve cell, alters the nerve cell's responses to external electrical stimuli.

In accordance with the principles of the present disclosure as embodied and as broadly described herein, a method for suppressing nerve cell (particularly C-fiber) action potentials is provided. According to the disclosure, a magnetic treatment device is placed at such a distance from a mammalian sensory neuron that the magnetic field of the treatment device reaches the sensory neuron. During such placement, and for a period thereafter, the nerve cell action potentials are suppressed.

The magnetic treatment devices may be comprised of four magnetic bodies having two positive and two negative magnetic poles in single or multiple planes, the magnet poles being oriented to define the four vertices of a symmetric quadrilateral shape in a three dimensional space, the two positive poles defining opposite diagonal vertices, and the two negative poles defining opposite diagonal vertices of the quadrilateral shape. Containment means are provided for holding the magnetic poles of the magnetic bodies in the quadrilateral orientation within a housing by embedding the magnet devices in the wall of the housing. The plurality of magnet bodies comprises four cylindrical magnetic bodies, each having one magnetic center charge face. It is necessary that two of the cylindrical magnetic bodies have a positive magnetic pole on one face and two of the magnetic bodies have a negative magnetic pole on one face, and that the two positive and two negative magnetic poles on the magnetically charged faces of the four magnet bodies be in the quadrilateral orientation described above. The proximity of the individual magnets within the device must be maintained. Separation of the individual magnets or bringing the device in close proximity to other magnets will cause interference with the magnetic field and will change the flux lines and gradient of the field so that the device will not effectively alter the C-fiber firing.

An exemplary implementation relates to a method for using quadripolar, circular, center charged, energy balanced magnetic devised in a four (4) magnet array of alternating polarity in which the magnetic poles are separated only by a distance which will allow a magnetic sphere of influence on all adjacent poles to suppress the firing of action potentials of mammalian sensory neurons. These magnetic arrays are placed in an epidural housing. They are placed in a helical array with the distance between magnetic clusters being 1 cm (a distance which breaks the sphere of influence, one cluster field to another). The cluster is rotated about 43 degrees in succession one cluster to the next. There is a difference in electrical potential across a cell membrane of sensory neurons. When a neuron receives an impulse transmitted from another nerve cell, the electrical potential difference across the membrane of the cell is dramatically reduced and generally reverses. This reduction and reversal of potential is referred to as the firing of the neurons action potential. If such action potential firings are suppressed, the transmissions of nerve impulses are also suppressed.

Pain sensations in the human body can be a result of improper nerve function, as when such pain is caused by inordinately excitable nerve cells or by nerve cells having cell wall membranes that leak ions. Pain sensations may also be caused by damaged nerve cells, as for example nerve cells suffering from post-operative scarring or physically impinged nerve cells commonly associated with degenerative disc disease. Even when nerves function properly, chronic pain sensations are initiated through nerve cells. Thus, new ways of altering nerve cell function, as for example by stabilizing nerve cell wall membranes, may lead to new therapies for the treatment of pain.

Accordingly, one implementation provides a method for applying a magnetic field which is particular to this device, to a nerve cell such that it alters nerve behavior. This disclosure relates to a method of applying the magnetic field to the dorsal root ganglia by placing the device in the epidural space adjacent to the dorsal root.

Another implementation provides a magnetic device with a configuration of static magnets with a particular pole design that, when placed close to a nerve cell, alters the nerve cell's responses to external electrical stimuli. In order to achieve the result on nerve cells, it is necessary that the proximity of the individual magnets within the device be maintained such that each pole exerts a sphere of magnetic influence on the other poles in the device. Any alteration of the proximity of the magnets one to another, with alternating polarity, will change the effect. Any alteration in the balance and symmetry of the power of each individual pole with respect to the other three poles may impair the effect upon the cell.

It will be apparent to those skilled in the art that the apparatus of this disclosure alters C-fiber firing both in vitro and in vivo.

G. Cardiac Dysfunction.

There is taught the methods, devices, techniques, and processes which specifically relate to symmetric magnetic devices such that the resultant steep field gradient is perpendicular to the site of action (membrane or neurons) and is of at least 1.5 mT for therapeutic application to mammals and more particularly to a static permanent quadripolar treatment device for placement in proximity to a mammal heart to control angina pectoris and cardiac dysrhythmia.

There is further taught the method which provides a device that alters myocardial behavior in a manner which stabilizes the electrical activity, dilates myocardial arteries, protects cells from cell death and controls chest pain which is secondary to ischemia. Another implementation is to provide a magnetic device that alters myocardial behavior in a manner which controls myocardial ischemia and chest pain.

There is further taught the method which provides a magnetic device that alters myocardial behavior by altering sodium and calcium channel function such that the quadripolar, alternating polarity and the subsequent field gradient block varying degrees of sodium and calcium channel function. The degree of blockage is related to the gradient and strength of the field. The gradient and the field strength may be manipulated by this technology.

There is further taught the method which provides an apparatus for applying a variable magnetic flux to the mammal body in the area of the heart by manipulating components, size and location of the apparatus.

Another implementation relates to magnetic devices for therapeutic application to the human body, and more particularly to a static permanent quadripolar treatment device for placement in proximity to the human heart to control angina pectoris (chest pain) and cardiac dysrhythmia. The three dimensional flux field gradient, when applied to the area of the heart which controls arrhythmia, improves blood flow, controls angina and protects ischemic myocardial muscle from cell death.

Another implementation of the device is effective in control of refractory angina pectoris and potentiates the effects of the pharmaceuticals, especially calcium channel blockers.

Accordingly, another implementation provides a device that alters myocardial behavior in a manner which stabilizes the electrical activity, dilates myocardial arteries, protects cells from cell death and controls chest pain which is secondary to ischemia.

Additional implementation is to provide a magnetic device that alters myocardial behavior in a manner which controls myocardial ischemia and chest pain.

In an exemplary implementation, a magnetic device that alters myocardial behavior by altering sodium and calcium channel function such that the quadripolar, alternating polarity and the subsequent field gradient block varying degrees of sodium and calcium channel function is provided. The degree of blockage is related to the gradient and strength of the field. The gradient and the field strength may be manipulated by this technology.

Another implementation provides an apparatus for applying a variable magnetic flux to the human body in the area of the heart by manipulating components, size and location of the apparatus.

H. Control of Pain and Sludging of Sickled Cells in Sickle Cell Disease.

There is taught the methods, devices, techniques, and processes which relate specifically to control of pain and sludging of sickled cells in sickle cell disease. Particularly a method which implements the disclosure to alter cell behavior in a manner that reduces sickle cell symptoms is taught.

In this implementation, a device that alters cell behavior in a manner which blocks or reverses the acute sickling process which leads to low oxygen carrying capacity and sludging of the sickled cells which causes pain and infection of major organs is provided. The device of the present disclosure also controls the pain which is associated with sickling.

The position of the devices is dictated by the location of the pain in sickle cell crisis. The device may be used prophylactically to prevent sickle cell symptoms.

Seizure/Movement Control Applications

In accordance as broadly described herein, a therapeutic static magnetic treatment device is adapted for placement of each device on the head of living mammals providing a symmetric three dimensional magnetic field such that the resultant steep field gradient is perpendicular to the site of action (membrane or neurons) and is of at least 1.5 mT. The 3 dimensional, steep gradient field created by the disclosure effectively stops neuronal discharge in the central nervous system and inhibits or reverses cerebral edema.

I. Seizure Control:

Another implementation relates to magnetic devices for therapeutic application to the human body, and more particularly to a quadripolar treatment device for placement on either the outside of the human head or implantable units for control of seizure disorders.

A further implementation provides a device that alters brain neuronal behavior in a manner which substantially stops the abnormal electrical discharge of the neurons, therefore stopping the seizures.

In an exemplary implementation, a magnetic device that alters brain neuronal behavior in a manner which substantially stops and controls drug resistant seizures.

Another implementation provides a method of applying a therapeutic magnetic device such that the resultant steep field gradient is perpendicular to the site of action (membrane or neurons) and is of at least 1.5 mT and relieve seizure in the mammal's head.

In a further implementation, a method of external attachment of the therapeutic quadripolar magnetic device to the area of the head, a method of implanting the device in the skull table and a method and apparatus for implanting the device intracerebrally is provided.

In a further implementation, the therapeutic quadripolar magnetic device may be implanted in the skull table or intracerebrally.

J. Treatment of Movement Disorders.

An exemplary implementation relates to magnetic devices for and methods for therapeutic application to the human body, and more particularly to a device for application of the human head in the area of the basal ganglia and/or application of a small implantable device to place in the appropriate location in the area of the basal ganglia.

In a further implementation, a device (and a method for its applications) which is adaptable to be applied to the skin of the head or may be implanted under stereotactic guidance into areas of the boral ganglia for the control of movement disorders, the device may be used either alone or in combination with medication, either to augment or to potentiate the drug effects.

Delay of Cell/Tissue Decay Applications

K. Protection of Transplant Organs.

There is taught the method which provides a device to better maintain cell integrity of transplantable organs by transporting them in a container equipped with a quadripolar magnetic flux generator which covers the organ with a step gradient quadripolar static magnetic flux field during transport.

In another implementation, a therapeutic static magnetic treatment device may be adapted for placement inside a human organ transplant transport cooler.

The current disclosure is designed to better maintain the cell integrity of the transplantable organ by transporting it in a container which is equipped with a quadripolar magnetic flux generator which covers the organ with a steep gradient, quadripolar, static magnetic flux field during transport. The field has been shown to possess the ability to offer significant protection from cell death.

In a further implementation, the magnetic field in a transport container for such organs as hearts, livers, kidneys, lungs and pancreases.

A major problem for the successful transplantation of freshly harvested organs is time from harvesting to transplantation. The organs are chilled in saline glucose in an attempt to slow metabolism and retard catabolism and shock of the organ. The efforts are not totally successful in preserving a good quality organ for transplant. There is need for a system which will better maintain the integrity of the organ such that it is delivered in optimal condition to the transplant recipient.

In exemplary implementations, the device better maintains the cell integrity of the transplantable organ by transporting it in a container which is equipped with a quadripolar magnetic flux generator which covers the organ with a steep gradient quadripolar static magnetic flux field during transport. This field has been shown to possess significant protection from death for isolated cells and organs in the laboratory.

L. Protection From Cell Injury and Death Following Neuronal Cell Insults Such as Contusion, Hypoxia, Stroke and Infection.

This application further reveals a method and technique for placement of the devices on the external body area overlying neuronal tissue such as brain, spinal cord and peripheral nerves following cell insults such as contusion, hypoxia, stroke, bleeding and infection.

An exemplary implementation relates to magnetic devices for therapeutic application to the human body, and more particularly to a quadripolar treatment device for placement on the human head, spinal cord or other accessible nervous tissue, to protect injured or insulted cells from cell death by providing a resultant steep field gradient that is perpendicular to the site of action (membrane or neurons) and is of at least 1.5 mT.

M. Magnetic Treatment Device for Treatment of Neurological Deficits Including Residual Encephalopathy Following Neurological Insults such as Strokes—For Protection From Cell Death and Dysfunction Following Hypoxic Injuries There is taught the methods, devices, techniques, and processes which relate specifically to protection from cell injury and death following neuronal cell insults such as contusion, hypoxia, stroke and infection. Also taught is application to the human body, and more particularly to a quadripolar treatment device for placement on the human head, spinal cord or other accessible nervous tissue, to protect injured or insulted cells from cell death.

An exemplary implementation relates to magnetic devices for therapeutic application to the human body and more particularly to a magnetic skull cap which utilizes appropriately placed quadripolar devices of the disclosure for placement on the human head for the application of several quadrilateral, steep, three dimensional magnetic flux steep field gradient devices.

An additional implementation of this disclosure is to provide neuro protection with the magnetic device as described both alone and to augment other agents such as drugs and hyperbaric oxygen both in humans and animal modles.

It is a further purpose of this disclosure to bring about protection from cell death, reduction of edema and reactivation of live but poorly functioning neuronal tissue in intracranial hemorrhage, strokes, hypoxic ischemicencephalopathy, brain contusions, encephalits, radiation therapy and spinal cord injuries.

A further implementation of this disclosure brings about protection from vasospastic phenomenon secondary to sub arachnoids hemorrhage. The vasospams results in delayed cerebral ischemia. A skull cap containing the symmetric three dimensional magnet with the steep field gradient that is perpendicular to the site of action (membrane or neurons) and is of at least 1.5 mT of this disclosure generates a magnetic flux field which blocks the vasospastic phenomenon.

Diagnostic Applications

1. Local Pain

Local pain is generated in the receptor field of the C-fibers which conduct painful impulses into the dorsal root entry zone and to higher centers where the impulse is interpreted as pain. C-fiber sympathetic efferent fibers are activated at the cord level and these fibers innervate the receptor field where the pain originates. These C-fiber efferents sensitize the somatic afferents. This sympathetic C-fiber efferent discharge into the receptor field brings about an increase of electrolyte and therefore increases the tissue conductance and decreases the resistance. This increased conductance in the skin, if properly interpreted, will allow the practitioners to determine the most effective locations for the quadripolar magnetic flux generator to be placed. When the magnetic flux generator of the disclosure is placed over the area of maximum conductance in a receptor field which corresponds to the local pain pattern, the C-fiber discharge is suppressed. Therefore, pain fiber impulse is blocked distally. In an exemplary implementation, once the area of maximum conductance is located, a second head will be rotated into place against the skin. This head will contain a quadripolar, alternating pole steep gradient magnetic flux generator and wiring means to stimulate electrically and magnetically. The magnetic gradient suppresses C-fiber firing and the electrical stimulator activates A-fiber firing in order to give instant confirmation of the correct location.

2. Radicular Pain

Radicular pain is generated by abnormal C-fiber discharge within the dorsal root. The symptoms are many such as compression, inflammation, hypoxia, contusion, and neuroproxia.

The dorsal division of the dorsal root is a small remnant in mammals and only innervates a narrow strip of tissue on either side of the spinal cord. This dorsal division of the dorsal root contains sympathetic efferent fibers in addition to somatic afferents.

These efferent fibers discharge into the receptor field, thereby increasing skin conductance. Therefore, in this instance areas of increased conductance of the skin superficial to the root are compatible with compression, radiculitis or other malfunction of the dorsal root. In an exemplary implementation, when an area of conductance increases twice the background is located, a second head of the device will be rotated into place against the skin. This head will contain a quadripolar, alternating pole, steep gradient magnetic flux generator and wiring means to stimulate electrically and magnetically the magnetic gradient suppresses C-fiber firing and the electrical stimulator activates A-firing in order to give instant confirmation of the correct location. The magnetic flux generator will suppress C-fiber firing directly and thereby reduce pain. The electrical stimulator will block C-fiber input into the central nervous system in the area of the substantiation.

Another implementation presents an electrical stimulator comprised of a pulse generator, controls for controlling the pulse frequency and morphology and an annular electrode system for both conductance reading and a second hear with an annular electrode for stimulation. The technology also provides for plastic containment means.

O. Potentiation of Pharmaceuticals and Focusing the Point of Maximum Therapy by Concentrating Drug to the Active Site.

An exemplary implementation relates to magnetic devices for therapeutic application to the human body, and more particularly to various sized magnetic devices for placement on the area of the human body in which drug potentiation is desired, such that the steep field gradient quadripolar field will interact with the drug, receptor or both.

There is taught the methods, devices, techniques, and processes which relate specifically to potentiation of pharmaceuticals and focusing the point of maximum therapy by concentrating drug to the active site.

There is further taught the methods, devices, techniques, and processes which relate specifically to magnetic devices for therapeutic application to the human body particularly to various sized magnetic devices for placement on the area of the human body in which drug potentiation is desired, such that the steep field gradient quadripolar field will interact with the drug and/or receptor.

There is further taught the methods which provides for potentiate the therapeutic effects at the receptor site.

There is further taught the methods which provides for use of magnetically compliant drugs which are thereby concentrated at the receptor area.

There is further taught the methods which potentiate the onset and intensity and duration of local anesthetics such as lidocaine when used as a dermally applied gel underneath the magnetic device for the purpose of bringing about rapid local anesthesia for minor procedures.

There is further taught the methods which place an intracranial quadripolar micro implant near an irritable focus to potentiate the effects of dilantin in the control of seizures which are drug resistant.

The use of pharmaceutical agents in medicine is at an all time high. Along with the desired effects, many drugs have significant side effects (undesirable effects) at the doses needed for the desired therapeutic effects. Another implementation potentiates the therapeutic effects at the receptor site, and in some instances in which magnetically compliant drugs are involved, the technology of this disclosure will concentrate the drug at the receptor area.

In a further implementation the device potentiates the onset and intensity and duration of local anesthetics such as lidocaine when used as a dermally applied gel underneath the magnetic device for the purpose of bringing about rapid local anesthesia for minor procedures.

In another implementation, the device is used to place an intracranial quadripolar micro implant near an irritable focus to potentiate the effects of dilantin in the control of seizures which are drug resistant.

Other Applications

Q. Control of Nausea and Vomiting Associated with Pregnancy, Motion and Chemotherapy.

This application reveals a method and technique for placement of the disclosure on the external body area over the vestibules apparatus and the distal medial radius area for the control of nausea and vomiting associated with pregnancy, motion and chemotherapy.

There is further taught the methods, devices, techniques, and processes which specifically relates to nausea and vomiting associated with pregnancy, motion and chemotherapy and also secondary to a variety of external stimuli.

An exemplary implementation relates to magnetic devices for therapeutic application to the human body and more particularly to a static magnetic quadripolar treatment device for placement on the human body such that the resultant steep field gradient is perpendicular to the site of action (membrane or neurons) and is of at least 1.5 mT for control of nausea and/or vomiting associated with pregnancy, motion sickness and chemotherapy.

While this disclosure has been described with emphasis on selected implementations, it should be understood that within the scope of the appended claims, the disclosure might be practiced or carried out in various ways other than as specifically described herein. In addition, many modifications may be made to adapt a particular situation, material, composition of matter, method, process step or steps, to the objective, spirit and scope of the present disclosure. All such modifications are intended to be within the scope of the claims appended hereto. In particular, while the methods disclosed herein have been described with reference to particular steps performed in a particular order, it will be understood that these steps may be combined, sub-divided, or re-ordered to form an equivalent method without departing from the teachings of the present disclosure. Accordingly, unless specifically indicated herein, the order and grouping of the steps is not a limitation of the present disclosure. The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein.

I claim:

1. A morphologically adaptable apparatus for altering a charge distribution upon living membranes with functional stabilization of a membrane physical electrical integrity, the apparatus comprising: a quadripolar, magnetic device in a four magnet array of alternating polarity in which each magnet of the array has a magnetic pole and generates a magnetic field and at least one of: i) a non-conductive fluid flux return medium below the magnetic array and ii) a conductive fluid flux focusing medium above and around the magnetic array, wherein the magnetic poles are separated by a predetermined distance which will provide an effective a magnetic sphere of influence at a desired site of action from the magnetic fields of all adjacent poles, and wherein the magnet array is altered to focus the magnetic sphere of influence at different depths.

2. The morphologically adaptable apparatus of claim 1, wherein the size of the magnets of the magnetic array can be altered to alter the location of the gradient of the magnetic field to set the steepest magnitude of the gradient at a sensory neuron.

3. The morphologically adaptable apparatus of claim 1 wherein the magnets are oriented to focus the magnetic field at a single point.

4. The apparatus in claim 1, wherein the apparatus comprises: i) the quadripolar, magnetic device in a four magnet array and the conductive fluid flux focusing medium, ii) the quadripolar, magnetic device in a four magnet array and the non-conductive fluid flux return medium or iii) the quadripolar, magnetic device in a four magnet array, the conductive fluid flux focusing medium and the non-conductive fluid flux return medium.

5. The apparatus of claim 4, wherein the conductive fluid flux focusing medium is molded in the form of a flux focusing ring.

6. The apparatus of claim 1, wherein the magnets are electromagnets.

7. A morphologically adaptable apparatus for altering a charge distribution upon living membranes with functional stabilization of a membrane physical electrical integrity, the apparatus comprising:
   a. a quadripolar, magnetic device in a four magnet array of alternating polarity in which each magnet of the array has a magnetic pole and generates a magnetic field, wherein the magnetic poles are separated by a predetermined distance which provides an effective 3-dimensional symmetric magnetic sphere of influence at a desired site of action from the magnetic fields of all adjacent poles;
   b. a conductive fluid flux focusing medium above and around the magnetic array; and
   c. a non-conductive fluid flux return medium below the magnetic array;
   and said effective 3-dimensional symmetric magnetic sphere of influence is perpendicular to the neuron current flow direction.

8. The morphologically adaptable apparatus of claim 7 wherein the magnetic field is at least 1.5 mT at the desired site of action.

9. The morphologically adaptable apparatus of claim 7, wherein the conductive fluid flux focusing medium comprises a gel material, such as copper compound conductive grease or grease filled with 80-95% silver.

10. The morphologically adaptable apparatus of claim 7, wherein the nonconductive fluid flux return medium comprises a gel, such as silicone gel or synthetic gels or greases filled with polymers such as polytetrafluoroethylene.

11. The morphologically adaptable apparatus of claim 7, defining a symmetric quadripolar, three dimensional magnetic flux field which is focused and balanced to the human body to stabilize excitable membranes and thereby reduce pain and edema associated with acute injury, inflammation or surgical procedure and to decrease wound healing time.

12. The apparatus of claim 7, wherein the conductive fluid flux focusing medium is molded in the form of a flux focusing ring.

13. The morphologically adaptable apparatus of claim 7, wherein the magnets are electromagnets.

14. A morphologically adaptable apparatus for altering a charge distribution upon living membranes with functional stabilization of the membrane physical electrical integrity, the apparatus comprising:
   d. a quadripolar, energy balanced magnetic device in a four magnet array of alternating polarity in which each magnet of the array has a magnetic pole and generates a magnetic field, wherein the magnetic poles are separated by a predetermined distance to define a most effective magnetic sphere of influence at a desired site of action from the magnetic fields of all adjacent poles; and
   e. a gel flux focusing medium surrounding the 4 magnet array on an outer perimeter stationed essentially midway between a top and bottom of the magnetic poles.

15. The morphologically adaptable apparatus of claim 14 further comprising a gel flux return medium away from the membrane surface for returning the magnetic flux thereby altering the strength and gradient without altering center charge symmetry and homogeneity of the 3-dimensional steep gradient field which is in contact with the membrane.

16. The morphologically adaptable apparatus of claim 14, wherein the magnets are electromagnets.

* * * * *